(12) United States Patent
Schweinsberg et al.

(10) Patent No.: US 9,743,663 B2
(45) Date of Patent: Aug. 29, 2017

(54) PELARGONIC ACID FORMULATION

(75) Inventors: Otto Schweinsberg, Rheinböllen (DE);
Arthur Ziegler, Kirsohroth (DE)

(73) Assignee: Compo GmbH & Co., KG, Munster (DE)

( * ) Notice: Subject to any disclaimer, the term of this patent is extended or adjusted under 35 U.S.C. 154(b) by 529 days.

(21) Appl. No.: 13/704,127

(22) PCT Filed: Jun. 22, 2011

(86) PCT No.: PCT/EP2011/060391
§ 371 (c)(1),
(2), (4) Date: Feb. 13, 2013

(87) PCT Pub. No.: WO2011/161133
PCT Pub. Date: Dec. 29, 2011

(65) Prior Publication Data
US 2013/0231247 A1 Sep. 5, 2013

(30) Foreign Application Priority Data

Jun. 24, 2010 (EP) .................................... 10167225
Dec. 30, 2010 (EP) .................................... 10197414

(51) Int. Cl.
*A01N 37/02* (2006.01)
(52) U.S. Cl.
CPC .................................. *A01N 37/02* (2013.01)
(58) Field of Classification Search
CPC ..................................................... A01N 37/02
See application file for complete search history.

(56) References Cited

U.S. PATENT DOCUMENTS

| 4,436,547 | A | * | 3/1984 | Sampson | A01N 25/32 |
| | | | | | 504/128 |
| 5,035,741 | A | * | 7/1991 | Puritch | A01N 37/02 |
| | | | | | 504/142 |
| 5,795,847 | A | * | 8/1998 | Nielsen | A01N 25/04 |
| | | | | | 504/206 |
| 5,919,733 | A | * | 7/1999 | Sedun | A01N 37/02 |
| | | | | | 504/320 |
| 5,985,798 | A | * | 11/1999 | Crudden | A01N 57/20 |
| | | | | | 504/206 |

FOREIGN PATENT DOCUMENTS

| EP | 0868849 A1 | 10/1998 |
| EP | 1589817 A1 | 11/2005 |
| GB | 2247621 A | 3/1992 |
| WO | 91/05472 A1 | 5/1991 |
| WO | 9105471 A1 | 5/1991 |
| WO | 9309669 A1 | 5/1993 |
| WO | 9703560 A1 | 2/1997 |
| WO | 0016620 A1 | 3/2000 |
| WO | 2004068948 A1 | 8/2004 |

OTHER PUBLICATIONS

The translation of the International Preliminary Report on Patentability issued in corresponding international application serial No. PCT/EP2011/060391 (11 pages).
English language translation of Written Opinion for PCT/EP2011/060391.
International Search Report for PCT/EP2011/060391(6 pages).

* cited by examiner

*Primary Examiner* — Johann R Richter
*Assistant Examiner* — Danielle Sullivan
(74) *Attorney, Agent, or Firm* — Saul Ewing, LLP; Peter C. Lauro, Esq.

(57) ABSTRACT

The present invention relates to a pelargonic acid formulation in the form of an oil-in-water emulsion and the use thereof for controlling undesired vegetation. The herbicidal pelargonic acid formulation according to the invention comprising:

a) as component A, pelargonic acid or a mixture of aliphatic $C_6$-$C_{10}$-carboxylic acids with a pelargonic acid content of at least 80% by weight based on the total weight of the mixture;
b) as component B, at least one organic solvent which under standard conditions has a water solubility of below 1 g/l and which has a boiling point of above 130° C. at standard pressure;
c) as component C, at least one surface-active substance which is selected among compounds of the formula I

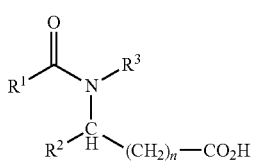

(I)

in which
n represents 0 or 1,
$R^1$ represents a linear or branched $C_6$-$C_{22}$-alkyl radical or a linear or branched $C_6$-$C_{22}$-alkenyl radical and
$R^2$ and $R^3$ independently of one another represent hydrogen or a $C_1$-$C_4$-alkyl group;
d) as component D, at least one nonionic surfactant which is selected among substances which include at least one poly-$C_2$-$C_4$-oxyalkylene group;
e) as component E, at least one amino acid with an isoelectric point in the range of from 5 to 7, and
f) water.

20 Claims, No Drawings

PELARGONIC ACID FORMULATION

RELATED APPLICATIONS

This application is the U.S. national phase, pursuant to 35 U.S.C. §371, of PCT international application Ser. No. PCT/EP2011/060391, filed Jun. 22, 2011, designating the United States and published on Dec. 29, 2011 as publication WO 2011/161133 A2, which claims priority to European application Ser. No. 10167225.1, filed Jun. 24, 2010 and European application Ser. No. 10197414.5, filed Dec. 30, 2010. The entire contents of the aforementioned patent applications are incorporated herein by this reference.

DESCRIPTION

The present invention relates to a pelargonic acid formulation in the form of an oil-in-water emulsion and its use for controlling undesired vegetation.

A host of different herbicides are used in agriculture, in industry and on domestic premises to control undesired weeds and other plants. Those based on synthetic active ingredients are traditionally the most effective and most frequently used herbicides. The problem is that, as a rule, the environmental compatibility of these highly-effective herbicides is low. Thus, they are frequently distinguished by poor biodegradability and/or high toxicity toward humans and animals, and they frequently lead to resistances in the weeds. These properties make such herbicides unsuitable precisely for the application on domestic premises, where they are applied not by experts, but by untrained operators.

Frequently, herbicides or other pesticides from naturally occurring substances such as fatty acids or salts of fatty acids have a markedly better biodegradability in comparison with compounds which are based on synthetic active substances. The toxicity of such herbicides toward humans, animals and nature is lower, too. However, these advantages are as a rule accompanied by a shorter duration of action.

Various herbicidal formulations based on salts of aliphatic carboxylic acids having 8 to 12 C atoms have recently been described.

Thus, aqueous formulations of herbicidal fatty acids which comprise substantial amounts of emulsifiers are known from WO 91/05471. Only relatively small pelargonic acid concentrations can be formulated stably in this manner. Likewise, nonaqueous concentrates which are composed essentially of this herbicidal fatty acid and the emulsifier are likewise disclosed in WO 91/05471. However, such formulations have a potent irritant effect on the skin and the eyes. The stability upon dilution is not satisfactory.

WO 91/05472 discloses nonaqueous formulations which are composed of a herbicidal fatty acid, a surface-active substance and an oil constituent from the group of the triglycerides, terpenoids and paraffinic mineral oils. Again, a disadvantage here is the potent irritant effect, since the carboxylic acids are not present in neutralized form. In addition, the stability upon dilution is not satisfactory.

GB 2247621, in turn, discloses aqueous formulations of herbicidal fatty acids which comprise the fatty acids in partially neutralized form. By way of cosolvent, the formulations comprise a volatile alcohol which evaporates upon use of the formulation. This is disadvantageous for work safety reasons.

WO 93/09669 describes aqueous formulations of organo-ammonium salts of herbicidal fatty acids such as, for example, the isopropylammonium salt, tryptamine salt, n-amylamine salt, n-hexylamine salt or sec-butylamine salt of pelargonic acid. These salts display a herbicidal activity which is supposedly comparable to that of the free pelargonic acid. Disadvantageous is the odor of such formulations, specifically in the case of alkylamine salts of low-molecular-weight alkylamines. Alkylamine salts with a hydrophobic alkyl radical, i.e. an alkyl radical with a higher molecular weight, in turn, are toxicologically problematic and are, as a rule, insufficiently biodegradable.

EP 0868849 describes a herbicide formulation which comprises, as active constituent, a partially hydrolyzed ammonium salt of a fatty acid, i.e. a mixture of the fatty acid with the respective fatty acid ammonium salt. This composition is effective against algae, liverwort, mosses and higher plants and allegedly results in a reduced development of soiling on stone or concrete surfaces treated therewith. In these formulations, the reduced development of soiling, as measured by the degree of soiling before cleaning operations and/or the effects of the weather, are accompanied by a reduced herbicidal efficacy of the formulation. Therefore, the composition only has an unsatisfactorily low activity against a series of harmful plants, even when applied at higher application rates.

EP 1589817 describes a herbicide formulation which comprises acetic acid and glycine in various weight ratios. The glycine enhances the herbicidal activity of the acetic acid, is nonpoisonous and nonirritant to the human body. However, owing to the acetic acid which is present therein, the formulation has an intensive and unpleasant odor. Owing to the potent irritant effect of acetic acid, the product is considerably irritating to the skin, the mucous membranes and in particular the eyes. In addition, the herbicidal activity of such formulations, in particular against older plants, is low. The application rates of such formulations are relatively high, which results in considerably higher packaging, logistics and transport costs.

In short, it can be said that the formulations of herbicidal fatty acids which are known to date have a series of disadvantages, such as, for example, a high irritant effect on human or animal tissue, an unpleasant odor, more or less pronounced staining as a result of residues, only moderate stability upon dilution, i.e. the formulations are liable to phase separation upon dilution with water, or a low herbicidal activity.

The present invention is based on the object of providing herbicidal active substance formulations which are nontoxic to humans and animals, are well tolerated by the environment and have good biodegradability, do not leave visual residues after application, are free from strong odors or are not irritant and display a high efficacy as a nonselective herbicide, in particular against algae, mosses and weeds. Moreover, it is intended that the formulations have good formulation properties such as, for example, high stability to phase separation upon stirring and high stability upon dilution.

Surprisingly, it has been found that these and further objects are solved by the pelargonic acid formulation defined hereinbelow.

Accordingly, the present invention relates to herbicidal pelargonic acid formulations in the form of oil-in-water emulsions, comprising:
a) as component A, pelargonic acid or a mixture of aliphatic $C_6$-$C_{10}$-carboxylic acids with a pelargonic acid content of at least 80% by weight based on the total weight of the mixture;

b) as component B, at least one organic solvent which under standard conditions has a water solubility of below 1 g/l and which has a boiling point of above 130° C. at standard pressure;
c) as component C, at least one surface-active substance which is selected among compounds of the formula I

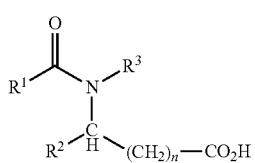

in which
n represents 0 or 1,
R$^1$ represents a linear or branched C$_6$-C$_{22}$-alkyl radical or a linear or branched C$_6$-C$_{22}$-alkenyl radical and
R$^2$ and R$^3$ independently of one another represent hydrogen or a C$_1$-C$_4$-alkyl group;
d) as component D, at least one nonionic surfactant which is selected among substances which include at least one poly-C$_2$-C$_4$-oxyalkylene group;
e) as component E, at least one amino acid with an isoelectric point in the range of from 5 to 7, and
f) water.

Further subject matter of the invention is the use of the pelargonic acid formulations according to the invention for controlling undesired vegetation.

Unless stated otherwise, the following general definitions apply within the scope of the present invention to the expressions used:

The expression C$_n$-C$_m$ in respect of the radicals to which it refers indicates the possible number of carbon atoms of these radicals.

"C$_1$-C$_4$-Alkyl" represents a linear or branched alkyl radical having 1 to 4 carbon atoms. These are methyl, ethyl, n-propyl, isopropyl, n-butyl, 2-butyl, isobutyl and tert-butyl.

"C$_1$-C$_{16}$-Alkyl" represents a linear or branched alkyl radical having 1 to 16 C atoms, for example "C$_1$-C$_4$-alkyl" as mentioned hereinabove or C$_5$-C$_{16}$-alkyl such as 1-pentyl, 2-pentyl, 3-pentyl, 2-methylbutyl, 3-methylbutyl, hexyl, heptyl, octyl, 2-ethylhexyl, nonyl, decyl, 2-propylheptyl, undecyl, isoundecyl, dodecyl, tridecyl, isotridecyl, tetradecyl, pentadecyl or cetyl.

"C$_6$-C$_{22}$-Alkyl" represents a linear or branched alkyl radical having 6 to 22 carbon atoms. These are, inter alia, hexyl, heptyl, octyl, 2-ethylhexyl, nonyl, decyl, 2-propylheptyl, undecyl, isoundecyl, dodecyl, tridecyl, isotridecyl, tetradecyl, pentadecyl, cetyl, heptadecyl, octadecyl, nonadecyl, eicosyl, henicosyl and docosyl.

"C$_6$-C$_{22}$-Alkenyl" represents a linear or branched, ethylenically mono- or polyunsaturated, for example 1- or 2-ethylenically unsaturated, alkenyl radical having 6 to 22 carbon atoms. These are, inter alia, hexenyl, heptenyl, octenyl, ethylhexenyl, nonenyl, decenyl, undecenyl, dodecenyl, tridecenyl, tetradecenyl, pentadecenyl, cetenyl, heptadecenyl, octadecenyl, nonadecenyl, eicosenyl, henicosenyl and docosenyl.

As component A, the formulations according to the invention comprise pelargonic acid or a mixture of aliphatic carboxylic acids having 6 to 10 carbon atoms with a pelargonic acid content of at least 80% by weight, in particular at least 90% by weight, based on the total weight of the mixture. Further aliphatic carboxylic acids which may be present in this mixture besides pelargonic acid are, for example, caproic acid, oenanthic acid, caprylic acid and capric acid. Preferred as component A are, besides pure pelargonic acid, mixtures of the abovementioned linear aliphatic carboxylic acids whose pelargonic acid content amounts to at least 90% by weight based on the mixture. Particularly preferred are pelargonic acid and mixtures of pelargonic acid with caprylic acid.

In a preferred embodiment, the formulation comprises essentially no herbicidal active substances other than component A. In this context, "essentially no" means less than 0.1% by weight based on the total weight of the formulation.

As component B, the formulations according to the invention comprise at least one organic solvent with a boiling point of above 130° C. These include hydrocarbons such as, for example, paraffins, oils such as, for example, vegetable oils, dialkyl alkanedicarboxylates, in particular C$_1$-C$_{16}$-dialkyl C$_3$-C$_{10}$-adkanedicarboxyates, and alkyl alkanecarboxylates, in particular C$_1$-C$_{16}$-alkyl C$_6$-C$_{22}$-alkanecarboxylates, with the two last-mentioned classes of substances and their mixture being preferred as component B. In particular, component B is composed to at least 90% by weight, preferably to at least 99% by weight based on the total weight of component B, of C$_1$-C$_{16}$-alkyl C$_6$-C$_{22}$-alkanecarboxylates or di-C$_1$-C$_{16}$-dialkyl C$_3$-C$_{10}$-alkanedicarboxylates or mixtures of these. Examples of suitable C$_1$-C$_{16}$-alkyl C$_6$-C$_{22}$-alkanecarboxylates according to the invention are in particular the esters of octanoic acid (caprylic acid) of decanoic acid (capric acid), of decanoic acid (lauric acid), of tetradecanoic acid (myristic acid), of hexadecanoic acid (palmitic acid), of octadecanoic acid (stearic acid), of eicosanoic acid (arachidic acid) and of docosanoic acid (behenic acid), such as, for example, methyl octanoate, isopropyl octanoate, tert-butyl octanoate, 2-ethylhexyl octanoate, octyl octanoate, dodecyl octanoate, hexadecyl octanoate, methyl decanoate, isopropyl decanoate, tert-butyl decanoate, 2-ethylhexyl decanoate, octyl decanoate, dodecyl decanoate, hexadecyl decanoate, methyl dodecanoate, isopropyl dodecanoate, tert-butyl dodecanoate, 2-ethylhexyl dodecanoate, octyl dodecanoate, dodecyl dodecanoate, hexadecyl dodecanoate, methyl tetradecanoate, isopropyl tetradecanoate, tert-butyl tetradecanoate, 2-ethylhexyl tetradecanoate, octyl tetradecanoate, dodecyl tetradecanoate, hexadecyl tetradecanoate, methyl hexadecanoate, isopropyl hexadecanoate, tert-butyl hexadecanoate, 2-ethylhexyl hexadecanoate, octyl hexadecanoate, dodecyl hexadecanoate, hexadecyl hexadecanoate, methyl octadecanoate, isopropyl octadecanoate, tert-butyl octadecanoate, 2-ethylhexyl octadecanoate, octyl octadecanoate, dodecyl octadecanoate, hexadecyl octadecanoate, methyl eicosanoate, isopropyl eicosanoate, tert-butyl eicosanoate, 2-ethylhexyl eicosanoate, octyl eicosanoate, dodecyl eicosanoate, hexadecyl eicosanoate, isopropyl docosanoate, tert-butyl docosanoate, 2-ethylhexyl docosanoate, octyl docosanoate, dodecyl docosanoate and hexadecyl docosanoate. Especially preferred as component B are C$_1$-C$_{12}$-alkyl C$_{10}$-C$_{22}$-alkanecarboxylates such as, for example, methyl octadecanoate, isopropyl dodecanoate, isopropyl tetradecanoate, isopropyl hexadecanoate, isopropyl octadecanoate, 2-ethylhexyl tetradecanoate, octyl tetradecanoate, 2-ethylhexyl hexadecanoate, octyl hexadecanoate, octyl octadecanoate, 2-ethylhexyl octadecanoate and their mixtures. Examples of di-C$_1$-C$_{16}$-dialkyl C$_3$-C$_{10}$-alkanedicarboxylates according to the invention are in particular esters of butanedioic acid (succinic acid), of pentanedioic acid (glutaric acid), of hexanedioic acid (adipic acid), such as, for example, dibutyl butanedioate, diisopropyl butanedioate, dihexyl butanedioate, di-2- ethylhexyl butanedioate, di-2-octyl butanedioate, dibutyl pentanedioate, diisopropyl pentanedioate, dihexyl pentanedioate, di-2-ethylhexyl pentanedioate, di-2-octyl pentanedioate, dibutyl hexanedioate, dihexyl hexanedioate, dioctyl hexanedioate, di-2-ethylhexyl hexanedioate and diisopropyl hexanedioate.

In preferred embodiments of formulations according to the invention, component B comprises at least one or more $C_6$-$C_{12}$-alkyl $C_{10}$-$C_{22}$-alkanecarboxylate(s) as components B1, such as, for example, 2-ethylhexyl decanoate, octyl decanoate, decyl decanoate, dodecyl decanoate, 2-ethylhexyl dodecanoate, octyl dodecanoate, decyl dodecanoate, dodecyl dodecanoate, 2-ethylhexyl tetradecanoate, octyl tetradecanoate, decyl tetradecanoate, dodecyl tetradecanoate, 2-ethylhexyl hexadecanoate, octyl hexadecanoate, decyl hexadecanoate, dodecyl hexadecanoate, 2-ethylhexyl octadecanoate, octyl octadecanoate, decyl octadecanoate, dodecyl octadecanoate, 2-ethylhexyl eicosanoate, octyl eicosanoate, dodecyl eicosanoate, hexadecyl eicosanoate, 2-ethylhexyl docosanoate, octyl docosanoate, decyl docosanoate and dodecyl docosanoate. Especially preferred as component B1 are the abovementioned 2-ethylhexyl esters, such as 2-ethylhexyl octadecanoate.

Preferred embodiments of formulations according to the invention, component B may furthermore, as additional constituent B2, comprise one or more $C_1$-$C_4$-alkyl $C_6$-$C_{18}$-alkanecarboxylic esters such as methyl octanoate, ethyl octanoate, n-propyl octanoate, isopropyl octanoate, n-butyl octanoate, tert-butyl octanoate, methyl decanoate, ethyl decanoate, n-propyl decanoate, isopropyl decanoate, n-butyl decanoate, tert-butyl decanoate, methyl dodecanoate, ethyl dodecanoate, n-propyl dodecanoate, isopropyl dodecanoate, n-butyl dodecanoate, tert-butyl dodecanoate, methyl tetradecanoate, ethyl tetradecanoate, n-propyl tetradecanoate, isopropyl tetradecanoate, n-butyl tetradecanoate, tert-butyl tetradecanoate, methyl hexadecanoate, ethyl hexadecanoate, n-propyl hexadecanoate, isopropyl hexadecanoate, n-butyl hexadecanoate, tert-butyl hexadecanoate, methyl octadecanoate, ethyl octadecanoate, n-propyl octadecanoate, isopropyl octadecanoate, n-butyl octadecanoate and tert-butyl octadecanoate. Particularly preferred as constituent B2 are the isopropyl esters of the abovementioned $C_6$-$C_{18}$-alkanecarboxylic acids. Particularly preferred are isopropyl tetradecanoate, isopropyl hexadecanoate and their mixtures.

Furthermore preferred are formulations according to the invention in which the weight ratio of component B to component A is in the range of from 1:1 to 1:6, preferably 2:3 to 1:5, especially 1:2 to 1:4.

Equally preferred are formulations according to the invention in which the weight ratio of component B1 to component B2 is in the range of from 2:1 to 50:1, preferably 3:1 to 20:1, in particular 4:1 to 12:1.

The total amount of component A based on the total amount of the constituents other than water of the formulations according to the invention is typically in the range of from 30 to 60% by weight, in particular in the range of from 35 to 58% by weight and specifically in the range of from 40 to 55% by weight.

The total amount of component B based on the total amount of the constituents other than water of the formulations according to the invention is typically in the range of from 10 to 30% by weight, in particular in the range of from 11 to 25% by weight and specifically in the range of from 12 to 20% by weight.

As component C, the formulations according to the invention comprise at least one compound of the formula I, a salt or a mixture of various compounds of the formula I

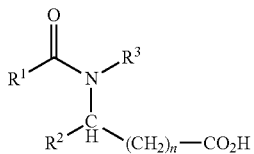

In formula I, $R^1$ represents a linear or branched $C_6$-$C_{22}$-alkyl or $C_6$-$C_{22}$-alkenyl radical. $R^2$ represents hydrogen or a $C_1$-$C_4$-alkyl group, preferably hydrogen. $R^3$ represents hydrogen or a $C_1$-$C_4$-alkyl group, preferably $C_1$-$C_4$-alkyl and in particular methyl. The variable n in particular represents 0.

Suitable salts of the compounds of the formula I are the alkali metal salts, for example the sodium or potassium salts, and the ammonium salts. Particularly suitable are the compounds of the formula I in the form of their free acid.

In preferred embodiments, component C of the formulations according to the invention comprises a component C1, which is at least one compound of the formula I in which $R^1$ represents a linear $C_{13}$-$C_{22}$-alkyl radical or a $C_{13}$-$C_{22}$-alkenyl radical. In particular, $R^1$ represents tetradecyl, pentadecyl, hexadecyl, heptadec-8-enyl, heptadecyl, octadecyl, nonadecyl, nonadec-10-enyl, nonadec-8-enyl, henicosyl and henicos-10-enyl. $R^2$ and $R^3$ independently of one another preferably represent hydrogen or $C_1$-$C_4$-alkyl, in particular hydrogen or methyl. The variable n in particular represents 0. In particular, $R^2$ represents hydrogen and $R^3$ represents methyl. Particularly preferred as component C1 is oleoyl-N-methylglycine (=N-oleoylsarcosine). Also suitable as component C1 are the salts of the abovementioned compounds of the formula I.

In a likewise preferred embodiments, component C of the formulations according to the invention comprises a component C2. This is at least one compound of the formula I or a salt thereof in which $R^1$ represents a linear $C_6$-$C_{12}$-alkyl radical or a $C_6$-$C_{12}$-alkenyl radical. In particular, $R^1$ represents undecyl. $R^2$ and $R^3$ independently of one another represent hydrogen or $C_1$-$C_4$-alkyl, specifically hydrogen or methyl. The variable n particularly represents 0. Especially preferred as component C2 is lauroyl-N-methylglycine (=N-lauroylsarcosine).

In further preferred embodiments, component C comprises at least one of the compounds of the formula I which have been mentioned as component C1 or a salt thereof, in particular one of the compounds mentioned in that place as being preferred, specifically N-oleoylsarcosine, and an additional component C2. This component C2 is at least one compound of the formula I or a salt thereof in which $R^1$ represents a linear $C_6$-$C_{12}$-alkyl radical or a $C_6$-$C_{12}$-alkenyl radical. In particular, $R^1$ represents undecyl. $R^2$ and $R^3$ independently of one another represent hydrogen or $C_1$-$C_4$-alkyl, specifically hydrogen or methyl. The variable n particularly represents 0. Especially preferred as component C2 is N-lauroylsarcosine.

The total amount of component C, based on the total amount of the constituents other than water of the formulations according to the invention, is typically in the range of from 1 to 20% by weight, in particular in the range of from 2 to 18% by weight and specifically in the range of from 3 to 15% by weight.

As component D, the formulations according to the invention comprise at least one nonionic surfactant which is selected among substances which include at least one poly- $C_2$-$C_4$-oxyalkylene group, in particular at least one polyoxyethylene group or at least one poly[oxyethylene-co-oxypropylene] group. Such surfactants usually include at least one, for example 1, 2 or 3, hydrocarbon radical(s) with, as a rule, at least 8 C atoms, for example 8 to 40 C atoms, to which one or more polyoxy-$C_2$-$C_4$-alkylenes are bonded. The hydrocarbon radicals may be alkyl groups, alkenyl groups having in each case 8 to 40, in particular 10 to 30, C atoms, cycloaliphatic groups, for example sterols, or araliphatic groups, for example $C_1$-$C_{16}$-alkylphenyl or tristyrylphenyl. Suitable hydrocarbon radicals may also be present in the form of mono-, di- or triglycerides, in which case they include 1, 2 or 3 alkyl or alkenyl groups which are derived from fatty acids. A polyoxy-$C_2$-$C_4$-alkylene group is understood as meaning an aliphatic polyether group which is composed of, on average, at least two, for example 2 to 100, oxyalkylene recurring units. Thus, polyoxy-$C_2$-$C_4$-alkylene groups consist of groups of the formula HO—[Z—O]$_n$— in which Z represents $C_2$-$C_4$-alkylene such as 1,2-ethanediyl, 1,2-propanediyl, 1-methyl-1,2-propanediyl and n indicates the number of recurring units in the polyoxy-$C_2$-$C_4$-alkylene group. The groups Z in these groups may be identical or different. Such surfactants are usually prepared by alkoxylating suitable alcohols, i.e. by reacting alcohols with one or more $C_2$-$C_4$-oxiranes ($C_2$-$C_4$-alkylene oxides), such as, for example, oxirane (ethylene oxide), propylene oxide, dimethyloxirane (isobutene oxide) ethyloxirane or a mixture of these.

Suitable surfactants of component D are, for example:
alkoxylated $C_1$-$C_{15}$-alkylphenols with a degree of alkoxylation in a range of from 2 to 100, preferably from 3 to 50, in particular from 3 to 30;
alkoxylated mono-, di- and tristyrylphenols with a degree of alkoxylation in a range of from 2 to 100, preferably from 5 to 50, in particular from 10 to 40;
alkoxylated $C_3$-$C_{22}$-alkanols and alkoxylated $C_8$-$C_{22}$-alkenols, in each case with a degree of alkoxylation in a range of from 2 to 100, preferably from 3 to 30, in particular from 4 to 20;
alkoxylated $C_8$-$C_{22}$-hydroxyalkanecarboxylic acids and $C_8$-$C_{22}$-hydroxyalkenecarboxylic acids with a degree of alkoxylation in a range of from 2 to 100, preferably from 5 to 50, in particular from 10 to 40;
alkoxylated $C_8$-$C_{22}$-alkylamines and $C_8$-$C_{22}$-alkenylamines with a degree of alkoxylation in a range of from 2 to 200, preferably from 3 to 50, in particular from 3 to 30;
alkoxylated mono- and diglycerides of aliphatic $C_8$-$C_{22}$-carboxylic acids (saturated or unsaturated fatty acids with 8 to 22 C atoms which optionally have a hydroxyl group attached to them) and alkoxylated sorbitan esters of aliphatic $C_8$-$C_{22}$-carboxylic acids with a degree of alkoxylation in a range of, as a rule, from 10 to 100, preferably from 15 to 70, in particular from 20 to 60;
alkoxylated triglycerides of aliphatic $C_8$-$C_{22}$-hydroxycarboxylic acids (saturated or unsaturated fatty acids with 8 to 22 C atoms which have OH groups attached to them) with a degree of alkoxylation in a range of, as a rule, from 10 to 100, preferably from 15 to 70, in particular from 20 to 60;
alkoxylated wool wax with a degree of alkoxylation in a range of from 10 to 100, preferably from 30 to 90, in particular from 40 to 85.

Among the abovementioned substances, the ethoxylates, i.e. the substances obtained by reaction with ethylene oxide, and the ethoxylate-co-propoxylates, in other words the reaction products of the abovementioned alcohols with ethylene oxide and propylene oxide, are preferred.

The degree of alkoxylation of the alkoxylated surfactants describes the average (number average) number of $C_2$-$C_4$-oxyalkylene groups, i.e. groups of the formula [Z—O] in polyoxy-$C_2$-$C_4$-alkylene groups which corresponds to the number of moles of $C_2$-$C_4$-oxirane per mole of OH groups of the alkoxylated compound.

In preferred formulations according to the invention, component D is selected among ethoxylated lanolin, poly-$C_2$-$C_4$-oxyalkylene $C_{10}$-$C_{20}$-alkyl ethers, ethoxylated mono-, di- and triglycerides of aliphatic $C_8$-$C_{22}$-hydroxycarboxylic acids, and their mixtures.

In preferred embodiments of formulations according to the invention, component D comprises ethoxylated lanolin, i.e. the reaction product of lanolin (wool wax) and ethylene oxide. In particular, component D comprises at least one ethoxylated lanolin with a degree of ethoxylation in the range of from 10 to 100, preferably 30 to 90, in particular 40 to 85.

In likewise preferred embodiments of formulations according to the invention, component D comprises at least one poly-$C_2$-$C_4$-oxyalkylene $C_{10}$-$C_{20}$-alkyl ether, preferably at least one polyoxyethylene $C_{10}$-$C_{20}$-alkyl ether and/or at least one poly(oxyethylene-co-oxypropylene)alkyl ether. The latter preferably has a degree of alkoxylation, in particular a degree of ethoxylation, in the range of from 2 to 20, preferably from 3 to 16, in particular from 4 to 10. Preferably, the alkyl radical has 12 to 16 C atoms. Particularly preferred among them are polyoxyethylene $C_{12}$-$C_{16}$-alkyl ethers having a preferably branched $C_{12}$-$C_{16}$-alkyl radical and a degree of ethoxylation in the range of from 2 to 20, preferably 3 to 16, in particular 4 to 10.

In likewise preferred embodiments of formulations according to the invention, component D comprises at least one alkoxylated, in particular ethoxylated, mono-, di- and triglyceride of aliphatic $C_8$-$C_{22}$-hydroxycarboxylic acids or a mixture thereof. This preferably has a degree of alkoxylation, in particular a degree of ethoxylation, in the range of from 10 to 100, preferably from 15 to 70, in particular from 20 to 60. In particular, it takes the form of an alkoxylated, in particular ethoxylated, castor oil (castor oil ethoxylate) or ethoxylated hydrogenated castor oil, which substances will, as a rule, have a degree of ethoxylation in the range of from 10 to 100, preferably from 15 to 70, in particular from 20 to 60.

In especially preferred embodiments of formulations according to the invention, component D comprises a mixture of ethoxylated lanolin (component D1) with at least one poly-$C_2$-$C_4$-oxyalkylene $C_{10}$-$C_{20}$-alkyl ether (component D2). In particular, component D comprises ethoxylated lanolin with a degree of ethoxylation in the range of from 10 to 100, preferably from 30 to 90, in particular from 40 to 85, and at least one poly-$C_2$-$C_4$-oxyalkylene $C_{10}$-$C_{20}$-alkyl ether, specifically at least one polyoxyethylene $C_{10}$-$C_{20}$-alkyl ether and/or at least one poly(oxyethylene-co-oxypropylene)alkyl ether with a degree of alkoxylation, in particular a degree of ethoxylation, in the range of from 2 to 20, preferably from 3 to 16, in particular from 4 to 10. In these embodiments, the weight ratio of component D1 to component D2 is preferably in the range of from 1:20 to 5:1 and in particular in the range of from 1:10 to 1:1.

In likewise specially preferred embodiments of formulations according to the invention, component D comprises a mixture of ethoxylated lanolin (component D1) with at least one substance selected among ethoxylated mono-, di- and triglycerides of aliphatic $C_8$-$C_{22}$-hydroxycarboxylic acids or their mixtures (component D3). In particular, component D comprises ethoxylated lanolin with a degree of ethoxylation in the range of from 10 to 100, preferably from 30 to 90, in particular from 40 to 85, and ethoxylated castor oil (castor oil ethoxylate) or ethoxylated hydrogenated castor oil, where the ethoxylated castor oil and the ethoxylated hydrogenated castor oil will, as a rule, have a degree of ethoxylation in the range of from 10 to 100, preferably from 15 to 70, in particular from 20 to 60. In these embodiments, the weight ratio of component D1 to component D3 is preferably in the range of from 1:20 to 5:1 and in particular in the range of from 1:10 to 1:1.

In a specific embodiment of formulations according to the invention, component D comprises an at least ternary mixture of the abovementioned components D1, D2 and D3. In this embodiment, the weight ratio of component D1 to component D3 is preferably in the range of from 1:20 to 5:1 and in particular in the range of from 1:10 to 1:1, and the weight ratio of D2 to component D3 is preferably in the range of from 1:20 to 5:1 and in particular in the range of from 1:10 to 1:1. In this case, the weight ratio of component D1 to D2 is preferably in the range of from 5:1 to 1:5, in particular in the range of from 3:1 to 1:3.

The total amount of component D, based on the total amount of the constituents other than water of the formulations according to the invention, is typically in the range of from 5 to 25% by weight, in particular in the range of from 8 to 22% by weight and specifically in the range of from 10 to 20% by weight.

Component E in the formulations according to the invention comprises at least one amino acid with an isoelectric point in the range of from 5 to 7. Examples of such amino acids are alanine, asparagine, aspartic acid, glutamine, glutaminic acid, glycine, isoleucine, leucine, lysine, methionine, phenylalanine, proline, serine, threonine, tryptophan, tyrosine and valine. Preferably, component E is selected from among alanine, glycine, isoleucine, leucine, proline, serine, threonine and valine. Component E is especially preferably glycine.

The total amount of component E based on the total amount of the constituents other than water in the formulations according to the invention, is typically in the range of from 3 to 20% by weight, in particular in the range of from 4 to 16% by weight and especially in the range of from 5 to 12% by weight.

In preferred embodiments of the invention, the formulations comprise components A to E in the following proportions:
a) 30 to 60% by weight of component A;
b) 10 to 30% by weight of component B;
c) 1 to 20% by weight of component C;
d) 5 to 25% by weight of component D and
e) 3 to 20% by weight of component E,
based on the total weight of the constituents other than water.

Especially preferably, the formulations according to the invention have the following composition:
a) 35 to 58% by weight of component A;
b) 11 to 25% by weight of component B;
c) 2 to 18% by weight of component C;
d) 8 to 22% by weight of component D and
e) 4 to 16% by weight of component E;
the information in % by weight referring in each case to the total weight of the formulation constituents other than water.

Especially preferably, the formulations according to the invention have the following composition:
a) 40 to 55% by weight of component A;
b) 12 to 20% by weight of component B;
c) 3 to 15% by weight of component C;
d) 10 to 20% by weight of component D and
e) 5 to 12% by weight of component E;
the information in % by weight referring in each case to the total weight of the formulation constituents other than water.

In an especially preferred embodiment 1 of the invention, the formulations comprise components A to E in the following proportions, based on the total weight of the constituents other than water:
a) 30 to 60% by weight, in particular 35 to 58% by weight and specifically 40 to 55% by weight, of component A;
b) 10 to 30% by weight, in particular 11 to 25% by weight and specifically 12 to 20% by weight, of component B, with the component comprising, or consisting of, at least one of the substances mentioned as component D1 and at least one of the substances mentioned as component B2;
c) 1 to 20% by weight, in particular 2 to 18% by weight and specifically 3 to 15% by weight, of component C, with component C comprising, or consisting of, at least one of the substances mentioned as component C1 and optionally one or more of the substances mentioned as component C2;
d) 5 to 25% by weight, in particular 8 to 22% by weight and specifically 10 to 20% by weight, of component D, with component D comprising, or consisting of, at least one of the substances mentioned as component D1 and at least one of the substances mentioned as component D2 and optionally one or more of the substances mentioned as component D3, and
e) 3 to 20% by weight, in particular 4 to 16% by weight and specifically 5 to 12% by weight, of component E.

In a likewise especially preferred embodiment 2 of the invention, the formulations comprise components A to E in the following proportions, based on the total weight of the constituents other than water:
a) 30 to 60% by weight, in particular 35 to 58% by weight and specifically 40 to 55% by weight, of component A;
b) 10 to 30% by weight, in particular 11 to 25% by weight and specifically 12 to 20% by weight, of component B, with the component comprising, or consisting of, at least one of the substances mentioned as component B1 and at least one of the substances mentioned as component B2;
c) 1 to 20% by weight, in particular 2 to 18% by weight and specifically 3 to 15% by weight, of component C, with component C comprising, or consisting of, at least one of the substances mentioned as component C2;
d) 5 to 25% by weight, in particular 8 to 22% by weight and specifically 10 to 20% by weight, of component D, with component D comprising, or consisting of, at least one of the substances mentioned as component D1 and at least one of the substances mentioned as component D2 and optionally one or more of the substances mentioned as D3, and
e) 3 to 20% by weight, in particular 4 to 16% by weight and specifically 5 to 12% by weight, of component E.

Preferably, the formulations according to the invention, in particular the formulations of the preferred embodiments and the formulations of the especially preferred embodiments and specifically the formulations of embodiments 1 and 2 comprise, as additional component G, at least one alkylpolyglucoside. Alkylpolyglucosides are understood as meaning compounds which include one or more, in particular one alkyl radical, in particular a $C_6$-$C_{22}$-alkyl radical, which is bonded via an oxygen atom to a mono- or oligosaccharide residue, for example to a mono-, di- or trisaccharide residue. The saccharide units here are typically derived from glucose. Preferred alkylglycosides are those which include on average 1 to 5, in particular 1 to 2, glucose units. As a rule, these will be mixtures. The amount of alkylpolyglucoside will, as a rule, not exceed 5% by weight and especially 1% by weight based on the total weight of the formulation and, if present, will typically amount to from 0.01 to 5% by weight, in particular from 0.1 to 1% by weight, based on the total weight of the formulation.

Preferably, the formulations according to the invention have a pH in the range of from 3 to 5.5, preferably in the range of from 3.8 to 5.2 and in particular in the range of from 4.2 to 5.0 (pH of the undiluted formulation, determined as specified in CIPAC MT 75.3).

Preferred embodiments of the formulations according to the invention relate to concentrates which typically comprise component A in a concentration of from 15 to 50% by weight, in particular from 20 to 40% by weight, based on the total weight of the formulation. Before being used as herbicides, these concentrates will typically be diluted at a concentration which is suitable for the desired use by diluting with water.

Further embodiments of the invention relate to formulations for direct application. These formulations can be employed directly, i.e. without being diluted any further. These formulations typically comprise component A at a concentration of from 0.1 to 5% by weight, frequently 1 to 5% by weight, based on the total weight of the formulation.

In addition, the formulations according to the invention may comprise further substances which are not directly connected to the purpose of the formulation, but which improve their applicability and/or practical properties. Examples therefor are, in particular, viscosity regulators (thickeners), preservatives, antifoams and antifreeze agents.

A person skilled in the art is familiar with such substances. The total amount of such substances will, as a rule, not exceed 10% by weight and in particular 1% by weight, based on the active substance concentrate, and, if present, will typically be in the range of from 0.01 to 10% by weight, in particular in the range of from 0.01 to 1% by weight, based on the total weight of the active substance concentrate.

The viscosity-modifying additives (viscosity regulators, thickeners or thickening agents) include in particular components which are known to impart, to aqueous formulations, pseudo plastic behavior, i.e. high viscosity at rest and low viscosity in the agitated state. Compounds which are suitable are, in principle, all those which are employed for this purpose in aqueous active substance concentrates. Substances which may be mentioned are, for example, inorganic substances such as bentonites or attapulgites (for example Attaclay® from Engelhardt). Other substances which may be mentioned are organic substances such as polysaccharides and heteropolysaccharides such as carrageenan, alginates, guaran and xanthan, for example the xanthan products sold under the trade names Kelzan® from Kelco and Rhodopol®, for example, the Rhodopol® types 23, 50MC, G, T and TG from Rhodia, with xanthan and modified xanthan preferably being used. The amount of the viscosity-modifying additives, if present, is frequently from 0.1 to 5% by weight based on the total weight of the formulations according to the invention.

Suitable antifoams are, for example, the silicone emulsions known for this purpose (Silikon® SRE, from Wacker or Rhodorsil® from Rhodia), long-chain alcohols, fatty acids, antifoams of the aqueous wax dispersion type, solid antifoams (known as "compounds"), organofluorine compounds and their mixtures. The amount of antifoam, if present, is frequently from 0.1 to 1% by weight based on the total weight of the formulations according to the invention.

Examples of preservatives are alkyl esters of para-hydroxybenzoic acid, sodium benzoate, 2-bromo-2-nitropropan-1,3-diol, ortho-phenylphenol, dichlorophene, benzyl alcohol hemiformal, pentachlorophenol, 2,4-dichlorobenzyl alcohol and, in particular, substituted isothiazolones such as, for example, $C_1$-$C_{10}$-alkylisothiazolinone, 5-chloro-2-methyl-4-isothiazolinone and benzoisothiazolinones, for example Proxel® from Avecia (or Arch), or the Acticide® types such as Acticide® RS or Acticide® B from Thor Chemie or the Kathon® types such as Kathon® MK from Rohm & Haas. The amount of preservatives, if present, is typically from 0.01 to 0.5% by weight, based on the total weight of the formulations according to the invention.

The formulations according to the invention may be prepared in a manner known per se analogously to the preparation of aqueous emulsions of oils. To this end, one will usually mix the constituents of the formulation with each other. As a rule, component D will be dissolved in water, the resulting solution will be mixed with components A, B and C, optionally with stirring, and component E and optionally further components will then be incorporated. These steps may be carried out at room temperature or at an elevated temperature, for example at temperatures in the range of from 20 to 90° C. and in particular at temperatures in the range of from 30 to 80° C. If the formulation comprises component G, it may be expedient to dissolve the latter in water, together with component D. The formulations according to the invention which are formulated for direct application may also be prepared by diluting the concentrates with water or an aqueous solution of components D and optionally G.

Further subject matter of the invention is the use of the formulations according to the invention for controlling undesired vegetation.

The herbicidal formulations according to the invention are suitable as nonselective herbicides for controlling algae, mosses and weeds, in particular weeds from the families Compositae, Crassulaceae, Hylocomiaceae, Marchantiacea, Poaceae, Chenopodiaceae, Polygonaceae, Umbelliferae, Cruciferae, Boraginaceae, Plantaginaceae, Rubiaceae, Geraniaceae and Chloroplastida, such as green algae, and hornworts, Liverworts and Bryophyta. In particular, the formulations according to the invention are suitable for controlling undesired vegetation such as mosses, algae and turf-borne weeds in turf and in borders with ornamental woody species. In this context, the formulation according to the invention acts selectively as a function of the use concentration and inflicts no, or hardly any, damage on turf and ornamental woody species. Furthermore, the formulation according to the invention is also particularly suitable for controlling undesired plants on paths and squares with or without tree stands.

The herbicidal formulations according to the invention will generally be applied in the form of an aqueous spray or watering mixture. To this end, the formulation is employed in a form suitable for application, with a component A content which is suitable for the desired application, for example a content of from 0.1 to 5% by weight.

The formulations according to the invention will typically be applied post-emergence, i.e. after the harmful plants have emerged.

For example, the ready-to-apply formulations may be applied by commercially available microsprayers, pressure sprayers or watering cans. In the post-emergence method, the formulation is sprayed or poured onto the undesired vegetation and subsequently allowed to act. Owing to the low-soiling properties, the area need not be cleaned after the treatment.

To widen the spectrum of action and to achieve synergistic effects, the herbicidal formulations according to the invention may, before application, be mixed, and applied together, with numerous other groups of herbicidal or growth-regulatory active substances, for example as a tank mix. In this context, the mixing partner will, as a rule, depend on the nature of the desired application. Examples of suitable mixing partners are, in particular, formulations of glyphosate and its salts such as glyphosate-potassium, glyphosate-sesquisodium, glyphosate-monoammonium, glyphosate-diammonium, glyphosate-dimethylammonium, glyphosate-isopropylammonium, glyphosate-trimesium, and formulations of maleic hydrazide and its salts.

Furthermore, it may be useful if, before application, the formulation according to the invention is mixed, and applied jointly, with further plant protection agents, for example with agents for controlling pests or phytopathogenic fungi and/or bacteria. Also of interest is the miscibility with mineral salt solutions which are employed for remedying nutritional and trace-element deficiencies.

The examples which follow are intended to illustrate the invention and are not to be construed as limiting.

A PREPARATION EXAMPLES

The following starting materials were used:
pelargonic acid: commercially available mixture of linear $C_8$-$C_{10}$-alkanecarboxylic acids with a pelargonic acid content of >90% by weight
2-ethylhexyl octadecanoate (Crodamol OS from Croda GmbH)
isopropyl tetradecanoate (tetradecyl myristate)
oleoyl-N-methylglycine (Crodasinic O from Croda GmbH)
lauroyl-N-methylglycine (Crodasinic L from Croda GmbH)
sodium lauroylsarcosinate, 30% by weight strength solution (Crodasinic LS 30 from Croda GmbH)
ethoxy-(75)-lanolin (Solan E from Croda GmbH)
ethoxylated isotridecanol, degree of ethoxylation 8-9 (Genapol X 080 from Clariant)
alkylpolyglycoside: $C_8$-$C_{10}$-alkylpolyglycoside with a degree of polymerization of 1.5, active content 50-70% by weight (Agnique PG 8105-G from Cognis GmbH)
biocide: 1,2-benzisothiazolon, 20% by weight strength (Acticide B20, Thor-Chemie)
castor oil (35)-polyethoxylate: ethoxylated castor oil with a degree of ethoxylation of 35. CAS-No. 61791-12-6 (Cremophor EL from BASF SE).

Example 1: Formulation as a Concentrate

To prepare a formulation according to the invention, 442.7 g of deionized water were introduced into a suitable vessel. 1.5 g of alkylpolyglycoside and 20 g of ethoxy-(75)-lanolin were dissolved therein, with stirring. Thereafter, the mixture was warmed to 50° C., 50 g of ethoxylated isotridecanol were added, and the mixture was stirred at 50° C. until a homogeneous aqueous solution was present. 270.7 g of pelargonic acid (90% strength), 80 g of 2-ethylhexyl octadecanoate, 10 g of isopropyl tetradecanoate and 75 g of oleoyl-N-methylglycine were mixed with each other. The resulting homogeneous mixture was incorporated at 50° C. into the homogeneous aqueous solution with stirring, whereby an aqueous emulsion was obtained. 40 g of glycine were incorporated at 50° C. into this aqueous emulsion, with stirring, until the glycine was dissolved. Thereafter, 10 g of a 30% by weight strength aqueous solution of sodium lauroylsarcosinate was added, with stirring, and the mixture was emulsified for 5 minutes in an Ultra-Turrax at 15 000 revolutions/minute. In this manner, a stable aqueous emulsion with a pelargonic acid content of 237.6 g/l and a pH of from 4.5 to 4.8 was obtained. It was possible to dilute the emulsion to the desired use concentration with water without any problems arising. Owing to its pH, it is not irritant to animal tissue. Even after 40 weeks' storage at 20-25° C., no separation of the emulsion as observed.

Example 2: Formulation as a Concentrate with Castor Oil (35)-Polyethoxylate 481.5 g of deionized water were introduced into a suitable vessel. 1.5 g of alkylpolyglycoside and 20 g of ethoxy-(75)-lanolin were dissolved therein, with stirring. Thereafter, the mixture was warmed to 50° C., 20 g of ethoxylated isotridecanol and 60 g of castor oil (35)-polyethoxylate were added, and the mixture was stirred at 50° C. until a homogeneous aqueous solution was present. 267 g of pelargonic acid (90% strength), 80 g of 2-ethylhexyl octadecanoate, 10 g of isopropyl tetradecanoate and 20 g of lauroyl-N-methylglycine were mixed with each other. The resulting homogeneous mixture was incorporated at 50° C. into the homogeneous aqueous solution with stirring, whereby an aqueous emulsion was obtained. 40 g of glycine were incorporated at 50° C. into this aqueous emulsion, with stirring, until the glycine was dissolved. Thereafter, the mixture was emulsified for 5 minutes in an Ultra-Turrax at 15 000 revolutions/minute. In this manner, a stable aqueous emulsion with a pelargonic acid content of 237.6 g/l and a pH of from 4.5 to 4.8 was obtained. It was possible to dilute the emulsion to the desired use concentration with water without any problems arising.

Examples 3 and 4: Formulation as a Concentrate

The concentrates of examples 3 and 4 were prepared analogously to example 1. The compositions of the formulations of examples 1 to 4 are specified in table 1.

TABLE 1

| | Example 1 | Example 2 | Example 3 | Example 4 |
|---|---|---|---|---|
| Pelargonic acid (90% strength) [% by weight] | 27.1 | 26.7 | 30 | 30 |
| 2-Ethylhexyl octadecanoate [% by weight] | 8.0 | 8.0 | 8.0 | 8.0 |
| Isopropyl tetradecanoate [% by weight] | 1.0 | 1.0 | 1.0 | 1.0 |
| Oleoyl-N-methylglycine [% by weight] | 7.5 | 0 | 8.0 | 6.0 |
| Lauroyl-N-methylglycine [% by weight] | 0 | 2.0 | 0 | 0 |
| Sodium lauroylsarcosinate* [% by weight] | 0.3 (1.0*) | 0 | 0 | 0.3 (1.0*) |
| Ethoxylated isotridecanol [% by weight] | 5.0 | 2 | 5.0 | 5.0 |

TABLE 1-continued

|  | Example 1 | Example 2 | Example 3 | Example 4 |
|---|---|---|---|---|
| Ethoxy-(75)-lanolin [% by weight] | 2.0 | 2 | 2.0 | 2.0 |
| Castor oil (35)-polyethoxylate [% by weight] | 0 | 6.0 | 0 | 0 |
| Glycine [% by weight] | 4.0 | 4.0 | 4.0 | 5.0 |
| Alkylpolyglycoside [% by weight] | 0.15 | 0.15 | 0.15 | 0.25 |
| Water [% by weight] | ad 100 | ad 100 | ad 100 | ad 100 |

*The value followed by * refers to the 30% by weight strength aqueous solution

Example 5: Formulation for Direct Application

To prepare a ready-to-apply form of the formulation according to the invention, 127.4 g of the formulation described in example 1 were diluted with an aqueous solution of 0.5 g of oleoyl-N-methylglycine and 0.5 g of a 20% strength 1,2-benzisothiazol-3(2H)-one composition in 872 ml of deionized water. The resulting formulation had a pelargonic acid content of 31 g/l and a pH of 4.5 to 5.0. Owing to its pH, it is not irritant to animal tissue. Even after 40 weeks' storage at 20-25° C., no separation of the formulation was observed.

B INVESTIGATION OF THE HERBICIDAL ACTIVITY

The herbicidal activity of the pelargonic acid formulations according to the invention against weeds was demonstrated by the following GEP field experiments:
All experiments were performed in accordance with the following EPPO Guidelines:
PP 1/117 (2) weeds in non-agricultural land
PP 1/136 (2) weeds in amenity grass land
PP-1/141 (2) weeds in tree and shrub nurseries
and treated post-emergence with the application rates mentioned in the use examples.
The experiments were evaluated on the basis of a scale from 0 to 100. In this context, 100 means no emergence of the plants, or complete destruction of at least the aerial parts, and zero means no damage, or normal course of growth. The weeds used were the plants listed in table 2:

TABLE 2

| Name (Latin) | Name (English) |
|---|---|
| Avena sterilis | Sterile oat |
| Achillea millefolium | Milfoil |
| Anthriscus sylvestris | Woodland beak chervil |
| Agropyron repens | Quackgrass |
| Bryophyta | mosses |
| Carduus acanthoides | Plumeless thistle |
| Chenopodium album | common lambsquarter |
| Cirsium arvense | creeping thistle |
| Cynodon dactylon | Bermuda grass |
| Dactylis glomerata | Orchard grass |
| Diplotaxis virgata | sand mustard |
| Echium creticum | — |
| Erigeron canadensis | Canada horseweed |
| Fallopia convolvulus | Black bindweed |
| Festuca rubra | red fescue |
| Filago arvensis | least cudweed |
| Funaria hygrometrica | Funaria hygrometrica |
| Geranium solandri | native geranium |
| Hieracium pilosella | mouse-ear hawkweed |
| Hypnum cupressiforme | Hypnum cupressiforme |
| Holcus lanatus | meadow soft grass |
| Marchantia polymorpha | star-liverwort |
| Melilotus alba | White sweet clover |
| Ornithopus compressus | Yellow seradella |
| Plantago lanceolata | Buckhorn plant |
| Poa annua | annual bluegrass |
| Poa pratensis | Kentucky bluegrass |
| Polygonum aviculare | knotgrass |
| Rhytidiadelphus squarrosus | Rhytidiadelphus squarrosus |
| Sanguisorba minor magnolii | — |
| Sedum acre | biting stonecrop |
| Senecio vulgaris | Common groundsel |
| Sherardia arvensis | field madder |
| Sonchus arvensis | Perennial sowthistle |
| Taraxacum officinale | common dandelion |
| Torillis arvensis | Spreading burparsley |
| Trigonella monspeliaca | Trigonella monspeliaca |
| Urtica dioica | Common nettle |
| Vicia villosa | Hairy vetch |

Application Example 1

The herbicidal activity of the formulation of example 3 and of various commercial formulations was tested on the weeds specified in tables 3, 4 and 5.

TABLE 3

| | Formulation | | | |
|---|---|---|---|---|
| | Example 3 | Example 3 | Comparative formulation 1 [1] | Comparative formulation 2 [2] |
| | | Application rate [3] | | |
| | 77 l/ha | 115 l/ha | 166 l/ha | 5 l/ha |
| | Time of assessment (DAT)[4] | | | |
| | 10 | 10 | 10 | 10 |
| Avena sterilis | 98.75 | 90 | 98.25 | 98.75 |
| Torillis arvensis | 98 | 98 | 92.25 | 20 |
| Ornithopus compressus | 100 | 100 | 100 | 43.75 |
| Diplotaxis virgata | 100 | 100 | 80 | 40 |
| Sanguisorba minor magnolii | 95 | 99 | 80 | 98.25 |
| Echium creticum | 85 | 90 | 20 | 50 |
| Cynodon dactylon | 99 | 99 | 70 | 95 |
| Plantago lanceolata | 99 | 98 | 85 | 30 |
| Sherardia arvensis | 100 | 100 | 100 | 30 |
| Weed mix | 97.25 | 99 | 83 | 60 |

[1] Commercially available pelargonic acid formulation: Finalsan Unkrautfrei, W. Neudorff GmbH KG, pelargonic acid 186.7 g/l pelargonic acid
[2] Commercially available glufosinate formulation: Finale, Bayer Cropscience S.L, ammonium glufosinate 15% by weight
[3] Application rate of formulation
[4] Days after treatment The herbicidal activity of the formulation according to the invention after ten days is at least equivalent to the prior art and in most cases superior.

TABLE 4

| | Formulation/application rate [2] | | | | | | | |
|---|---|---|---|---|---|---|---|---|
| | Example 3 115 l/ha | | | | Comparative formulation 1 [1] 166 l/ha | | | |
| | Time of assessment (DAT)[3] | | | | | | | |
| Weed species | 4 | 8 | 26 | 47 | 4 | 8 | 26 | 47 |
| Geranium solandri | 100 | 100 | 100 | 97.50 | 100 | 100 | 98.75 | 98.75 |
| Hieracium pilosella | 92.5 | 90.5 | 88.75 | 85 | 87.50 | 83.75 | 71.25 | 51.25 |
| Taraxacum officinale | 96.25 | 90 | 73.75 | 48.75 | 90 | 87.50 | 60 | 31.25 |
| Erigeron canadensis | 61.25 | 70 | 78.75 | 100 | 67.50 | 68.75 | 56.25 | 100 |
| Sedum acre | 83 | 81.25 | 58.75 | 61.25 | 77.50 | 73.75 | 56.25 | 52.5 |
| Holcus lanatus | 98.75 | 98.75 | 91.25 | 95 | 91.25 | 88.75 | 80 | 76.25 |
| Filago arvensis | 100 | 100 | 100 | 100 | 81.25 | 78.75 | 82.50 | 68.75 |
| Cirsium arvense | 100 | 97.50 | 91.25 | 95 | 100 | 100 | 85 | 70 |
| Rhytidiadelphus squarrosus | 100 | 100 | 98.75 | 72.50 | 100 | 100 | 83.75 | 66.25 |
| Festuca rubra | 77.50 | 73.75 | — | 53.75 | 87.50 | 93.75 | — | 23.75 |

[1] Commercially available pelargonic acid formulation: Finalsan Unkrautfrei, W. Neudorff GmbH KG, pelargonic acid 186.7 g/l pelargonic acid
[2] Application rate of the formulation
[3] Days after treatment

TABLE 5

| | Formulation/application rate [2] | | | | | |
|---|---|---|---|---|---|---|
| | Example 3 107 l/ha | | | Comparative formulation 1 [1] 166 l/ha | | |
| | Time of assessment (DAT) [3] | | | | | |
| Weed species | 7 | 20 | 90 | 7 | 20 | 90 |
| Marchantia polymorpha | 92.50 | 92 | 90.5 | 78.75 | 86.25 | 86.25 |
| Bryophyta | 97.50 | 100 | 100 | 91.25 | 100 | 100 |
| Poa annua | 91.25 | 94.75 | | 91.25 | 96.75 | |
| Chenopodium album | 91.25 | 95 | | 92.50 | 100 | |
| Polygonum aviculare | 96.25 | 100 | | 100 | 100 | |

[1] Commercially available pelargonic acid formulation: Finalsan Unkrautfrei, W. Neudorff GmbH KG, pelargonic acid 186.7 g/l pelargonic acid
[2] Application rate of the formulation
[3] Days after treatment This investigation demonstrates that not only the short-term efficacy of the formulation according to the invention after 4 and 7 days and its long-term efficacy after 47 and 90 days is in most cases superior to the efficacy of commercially available pelargonic acid formulations even at a lower application rate of the formulation.

Application Example 2

The herbicidal activity of the formulation of example 4 and a commercial pelargonic acid formulation was tested on the weeds specified in table 6.

TABLE 6

| | Formulation/application rate [2] | | | | | |
|---|---|---|---|---|---|---|
| | Example 4 107 l/ha | | | Comparative formulation 1 [1] 166 l/ha | | |
| | Time of assessment (DAT) [3] | | | | | |
| Weed species | 2 | 6 | 20 | 2 | 6 | 20 |
| Hieracium pilosella | 100 | 96 | 86.25 | 100 | 95 | 65 |
| Erigeron canadensis | 100 | 100 | 88.75 | 100 | 96.25 | 85 |
| Filago arvensis | 75 | 75 | 41.25 | 75 | 75 | 63.75 |
| Sedum acre | 93.75 | 93.75 | 75 | 92.5 | 86.25 | 52.5 |
| Taraxacum officinale | 96.25 | 88.75 | 53.75 | 91.25 | 90 | 45 |
| Rhytidiadelphus squarrosus | 98.75 | 72.50 | 53.75 | 100 | 70 | 32.50 |
| Bryophyta | 100 | 100 | 98.75 | 100 | 100 | 100 |

[1] Commercially available pelargonic acid formulation: Finalsan Unkrautfrei, W. Neudorff GmbH KG, pelargonic acid 186.7 g/l pelargonic acid
[2] Application rate of the formulation
[3] Days after treatment Application Example 3

The herbicidal activity of the formulation of example 2 and a commercial pelargonic acid formulation was tested on the weeds specified in table 7, 8, 9, 10 and 11.

TABLE 7

| | Formulation | | | | | | | |
|---|---|---|---|---|---|---|---|---|
| | Example 2 | | | | Comparative formulation 1 [1] | | | |
| | Application rate [2] | | | | | | | |
| | 130 l/ha | | | | 166 l/ha | | | |
| | Time of assessment (DAT) [3] | | | | | | | |
| | 3 | 11 | 30 | 50 | 3 | 11 | 30 | 50 |
| Anthriscus sylvestris | 30.0 | 30.0 | 25.0 | 25.0 | 30.0 | 30.0 | 22.5 | 22.5 |
| Carduus acanthoides | 92.5 | 96.5 | 90.0 | 90.0 | 93.7 | 97.0 | 90.0 | 90.0 |
| Dactylis glomerata | 99.0 | 99.0 | 99.0 | 99.0 | 99.0 | 99.0 | 99.0 | 99.0 |
| Hypnum | 99.0 | 99.0 | 99.0 | 99.0 | 99.0 | 99.0 | 99.0 | 99.0 |

TABLE 7-continued

| | Formulation | | | | | | | |
|---|---|---|---|---|---|---|---|---|
| | Example 2 | | | | Comparative formulation 1 [1] | | | |
| | Application rate [2] | | | | | | | |
| | 130 l/ha | | | | 166 l/ha | | | |
| | Time of assessment (DAT) [3] | | | | | | | |
| | 3 | 11 | 30 | 50 | 3 | 11 | 30 | 50 |
| cupressiforme | | | | | | | | |
| Melilotus alba | 99.0 | 99.0 | 90.0 | 90.0 | 99.0 | 99.0 | 90.0 | 90.0 |
| Poa pratensis | 99.0 | 99.0 | 99.0 | 99.0 | 99.0 | 99.0 | 99.0 | 99.0 |
| Trigonella monspeliaca | 99.0 | 99.0 | 94.0 | 94.0 | 99.0 | 99.0 | 92.0 | 92.0 |
| Vicia villosa | 99.0 | 99.0 | 99.0 | 99.0 | 99.0 | 99.0 | 99.0 | 99.0 |

[1] Commercially available pelargonic acid formulation: Finalsan Unkrautfrei, W. Neudorff GmbH KG, pelargonic acid 186.7 g/l pelargonic acid
[2] Application rate of formulation
[3] Days after treatment

TABLE 8

| | Formulation | | | | | | | |
|---|---|---|---|---|---|---|---|---|
| | Example 2 | | | | Comparative formulation 1 [1] | | | |
| | Application rate [2] | | | | | | | |
| | 130 l/ha | | | | 166 l/ha | | | |
| | Time of assessment (DAT) [3] | | | | | | | |
| | 3 | 10 | 25 | 45 | 3 | 10 | 25 | 45 |
| Achillea millefolium | 95.0 | 99.0 | 99.0 | 99.0 | 96.5 | 99.0 | 99.0 | 99.0 |
| Funaria hygrometrica | 93.0 | 96.3 | 99.0 | 99.0 | 95.0 | 99.0 | 99.0 | 99.0 |
| Taraxacum officinale | 95.0 | 97.3 | 97.8 | 98.5 | 96.3 | 99.0 | 99.0 | 99.0 |
| Urtica dioica | 95.0 | 99.0 | 99.0 | 99.0 | 96.0 | 99.0 | 99.0 | 99.0 |

[1] Commercially available pelargonic acid formulation: Finalsan Unkrautfrei, W. Neudorff GmbH KG, pelargonic acid 186.7 g/l
[2] Application rate of formulation
[3] Days after treatment

TABLE 9

| | Formulation | | | | | | | |
|---|---|---|---|---|---|---|---|---|
| | Example 2 | | | | Comparative formulation 1 [1] | | | |
| | Application rate [2] | | | | | | | |
| | 130 l/ha | | | | 166 l/ha | | | |
| | Time of assessment (DAT) [3] | | | | | | | |
| | 3 | 10 | 22 | 44 | 3 | 10 | 22 | 44 |
| Elytrigia repens | 32.5 | 78.8 | 78.8 | 67.5 | 8.8 | 78.8 | 81.3 | 93.8 |
| Sonchus arvensis | 80.0 | 80.0 | 72.5 | 66.3 | 5.0 | 98.8 | 98.8 | 99.5 |

[1] Commercially available glufosinate formulation: Finale, Bayer Cropscience S.L, ammonium glufosinate 15% by weight
[2] Application rate of formulation
[3] Days after treatment

TABLE 10

| | Formulation | | | | | |
|---|---|---|---|---|---|---|
| | Example 2 | | | Comparative formulation 1 [1] | | |
| | Application rate [2] | | | | | |
| | 130 l/ha | | | 166 l/ha | | |
| | Time of assessment (DAT) [3] | | | | | |
| | 2 | 9 | 28 | 3 | 9 | 28 |
| Funaria hygrometrica | 71.3 | 82.5 | 80.0 | 63.8 | 75.0 | 81.3 |
| Poa annua | 62.5 | 70.0 | 80.0 | 42.5 | 62.5 | 71.3 |
| Fallopia convolvulvus | 63.8 | 75.0 | 80.0 | 67.5 | 70.0 | 75.0 |
| Senecio vulgaris | 47.5 | 67.5 | 72.5 | 37.5 | 61.5 | 65.0 |

[1] Commercially available pelargonic acid formulation: Finalsan Unkrautfrei, W. Neudorff GmbH KG, pelargonic acid 186.7 g/l
[2] Application rate of formulation
[3] Days after treatment

TABLE 11

| | Formulation | | | | | | | |
|---|---|---|---|---|---|---|---|---|
| | Example 2 | | | | Comparative formulation 1 [1] | | | |
| | Application rate [2] | | | | | | | |
| | 90 l/ha (pouring) | | | | 166 l/ha (pouring) | | | |
| | Time of assessment (DAT) [3] | | | | | | | |
| | 10 | 14 | 23 | 42 | 10 | 14 | 23 | 42 |
| Hieracium pilosella | 72.5 | 77.5 | 53.8 | 35.0 | 47.5 | 62.5 | 37.5 | 20.0 |
| Rhytidiadelphus squarrosus | 77.0 | 83.3 | 87.8 | 93.3 | 66.3 | 77.0 | 84.3 | 88.8 |

[1] Commercially available pelargonic acid formulation: Bayer Garten, Rasen Moosfrei, pelargonic acid 186.7 g/l
[2] Application rate of formulation
[3] Days after treatment

We claim:

1. A herbicidal pelargonic acid formulation, which is an oil-in-water emulsion, comprising:
   a) 30 to 60% by weight of component A selected from the group consisting of pelargonic acid and mixtures of aliphatic $C_6$-$C_{10}$-carboxylic acids with a pelargonic acid content of at least 80% by weight based on the total weight of the mixture;
   b) 10 to 30% by weight of component B, wherein component B consists of one or more C6-C12-alkyl-C10-C22-alkanecarboxylic acid esters (B1) and one or more C1-C4-alkyl-C6-C18-alkanecarboxylic acid esters (B2), wherein said alkane carboxylic acid esters are organic solvents which under standard conditions have a water solubility of below 1 g/l and which have a boiling point of above 130° C. at standard pressure, and wherein component B is selected from the group consisting of $C_1$-$C_{16}$-alkyl-$C_6$-$C_{22}$-alkanecarboxylic acid esters, di-$C_1$-$C_{16}$-dialkyl-$C_3$-$C_{10}$-alkanedicarboxylic acid esters and mixtures thereof, wherein the weight ratio of component B1 to component B2 is in the range of from 2:1 to 50:1;
   c) 1 to 20% by weight of component C, wherein component C consists of at least one surface-active substance selected from the group consisting of compounds of the formula I

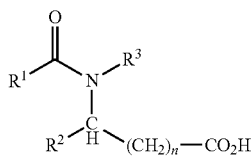

in which n represents 0 or 1,

R¹ represents a linear or branched $C_6$-$C_{22}$-alkyl radical or a linear or branched $C_6$-$C_{22}$-alkenyl radical and R² and R³ independently of one another represent hydrogen or a $C_1$-$C_4$-alkyl group;

d) 5 to 25% by weight of component D, wherein component D consists of at least one nonionic surfactant selected from the group consisting of substances that include at least one poly-$C_2$-$C_4$-oxyalkylene group;

e) 3 to 20% by weight of component E, wherein component E consists of at least one amino acid with an isoelectric point in the range of from 5 to 7, based on the total weight of the components A, B, C, D, and E other than water; and f) water.

2. The formulation as claimed in claim 1, where the formulation has a pH of from 3 to 5.5.

3. The formulation of claim 1, where the weight ratio of component B to component A is in the range of from 1:1 to 1:6.

4. The formulation of claim 1, wherein component C is at least one compound C1 of the formula I or a salt thereof in which R¹ represents $C_{13}$-$C_{22}$-alkyl or $C_{13}$-$C_{22}$-alkenyl, R² represents hydrogen and R³ represents methyl.

5. The formulation of claim 4, wherein component C is at least one compound C2 of the formula I or a salt thereof in which R¹ represents $C_6$-$C_{12}$-alkyl or $C_6$-$C_{12}$-alkenyl, R² represents hydrogen and R³ represents methyl.

6. The formulation of claim 1, where component C is selected from the group consisting of compounds of the formula I and salts thereof, in which R¹ represents $C_6$-$C_{12}$-alkyl or $C_6$-$C_{12}$-alkenyl, R² represents hydrogen and R³ represents methyl.

7. The formulation of claim 1, where component D is selected from the group consisting of ethoxylated lanolin, poly-$C_2$-$C_4$-oxyalkylene $C_{10}$-$C_{20}$-alkyl ethers, ethoxylated mono-, di- and triglycerides of aliphatic $C_8$-$C_{22}$-hydroxycarboxylic acids and mixtures thereof.

8. The formulation of claim 1, wherein component E is selected from the group consisting of glycine, alanine, valine, leucine, isoleucine, proline, threonine and serine.

9. The formulation of claim 1, comprising
a) 30 to 60% by weight of component A;
b) 10 to 30% by weight of component B, wherein component B consists of at least one $C_6$-$C_{12}$-alkyl-$C_{10}$-$C_{22}$-alkanecarboxylic acid ester and at least one $C_1$-$C_4$-alkyl-$C_6$-$C_{18}$-alkanecarboxylic acid ester;
c) 1 to 20% by weight of component C, wherein component C consists of at least one compound of the formula I in which R¹ represents $C_{13}$-$C_{22}$-alkyl or $C_{13}$-$C_{22}$-alkenyl, R² represents hydrogen and R³ represents methyl, or a salt thereof;
d) 5 to 25% by weight of component D, wherein component D consists of ethoxylated lanolin and at least one poly-$C_2$-$C_4$-oxyalkylene-$C_{10}$-$C_{20}$-alkyl ether;
e) 3 to 20% by weight of component E,
based on the total weight of the components other than water.

10. The formulation of claim 1, comprising
a) 30 to 60% by weight of component A;
b) 10 to 30% by weight of component B, wherein component B consists of at least one $C_6$-$C_{12}$-alkyl-$C_{10}$-$C_{22}$-alkanecarboxylic acid ester and in addition at least one $C_1$-$C_4$-alkyl-$C_6$-$C_{18}$-alkanecarboxylic acid ester;
c) 1 to 20% by weight of component C, wherein component C consists of at least one compound of the formula I in which R¹ represents $C_6$-$C_{12}$-alkyl or $C_6$-$C_{12}$-alkenyl, R² represents hydrogen and R³ represents methyl, or a salt or mixture thereof;
d) 5 to 25% by weight of component D, wherein component D consists of ethoxylated lanolin and at least one poly-$C_2$-$C_4$-oxyalkylene-$C_{10}$-$C_{20}$-alkyl ether;
e) 3 to 20% by weight of component E,
based on the total weight of the components other than water.

11. The formulation of claim 1, further comprising component G, wherein component G consists of at least one alkylpolyglucoside.

12. The formulation of claim 1, comprising component A in an amount of from 15 to 50% by weight based on the total weight of the formulation, wherein the formulation is in the form of a concentrate.

13. The formulation of claim 1 in a form which is suitable for application, comprising component A in an amount of from 0.1 to 5% by weight based on the total weight of the formulation.

14. The formulation of claim 1, comprising no herbicidal active substances other than component A.

15. A method for controlling undesired vegetation which comprises applying a formulation of claim 1 to undesired vegetation, thereby controlling undesired vegetation.

16. The method of claim 15, wherein the formulation is applied in form of an aqueous spray or watering mixture.

17. The method of claim 15, wherein the formulation is applied post emergence of the undesired vegetation.

18. The method of claim 15, wherein the undesired vegetation is selected from the group consisting of algae, mosses and weeds.

19. The method of claim 15, wherein the undesired vegetation is a member of a family selected from the group consisting of Compositae, Crassulaceae, Hylocomiaceae, Marchantiacea, Poaceae, Chenopodiaceae, Polygonaceae, Umbelliferae, Cruciferae, Boraginaceae, Plantaginaceae, Rubiaceae, Geraniaceae, Chloroplastida and Bryophyta.

20. The method of claim 15, wherein the undesired vegetation is selected from the group consisting of green algae, hornworts and liverworts.

* * * * *